(12) United States Patent
Tu et al.

(10) Patent No.: US 7,087,252 B2
(45) Date of Patent: Aug. 8, 2006

(54) **MEDICINAL PREPARATION CONTAINING PHENYLETHANOID GLYCOSIDES EXTRACTED FROM HERBACEOUS PLANT, *CISTANCHE TUBULOSA (SCHRENK.) WIGHT,* PROCESS OF MAKING THE SAME, AND USES OF THE SAME**

(75) Inventors: Pengfei Tu, Peking (CN); Zhihong Song, Peking (CN); Li Lei, Peking (CN)

(73) Assignee: Sinphar Pharmaceutical Co., Ltd., Taipei (TW)

( * ) Notice: Subject to any disclaimer, the term of this patent is extended or adjusted under 35 U.S.C. 154(b) by 471 days.

(21) Appl. No.: 10/618,740

(22) Filed: Jul. 15, 2003

(65) Prior Publication Data

US 2004/0162246 A1 Aug. 19, 2004

(30) Foreign Application Priority Data

Feb. 18, 2003 (TW) .............................. 92103351 A

(51) Int. Cl.
*A01N 65/00* (2006.01)

(52) U.S. Cl. .................................................... 424/725
(58) Field of Classification Search ................. 424/725
See application file for complete search history.

(56) References Cited

OTHER PUBLICATIONS

Carlos Jimenez et. al., *Phenylethanoid Glycosides In Plants: Structure and Biological Activity*, pp. 591-606, Nat. Prod. Rep., 1994.

F. Cometa et. al., *Phenylpropanoid glycosides. Distribution and pharmacological activity*, pp. 195-217, Fitoterapia, vol. LXIV, No. 3, 1993.

Hiromi Kobayashi et. al., *New Phenylethanoid Glycosides from Cistanche tubulosa (SCHRENK) Hook. f.* I., 1987, pp. 3309-3314, Chemical and Pharmaceutical Bulletin, vol. 35, No. 8 (Tokyo).

Fumio Yoshizawa et. al., *The Constituents of Cistanche tubulosa (SCHRENK) Hook. f. II. Isolation and Structure of a New Phenylethanoid Glycoside and a New Neolignan Glycoside,* Jul. 1990, pp. 1927-1930, Chemical and Pharmaceutical Bulletin, vol. 38, No. 7 (Tokyo).

Mansoor Ahmad et. al., *Acteoside: a New Antihypertensive Drug,* 1995, pp. 525-527, Phytotherapy Research, vol. 9, No. 7.

*Primary Examiner*—Michael Meller
(74) *Attorney, Agent, or Firm*—Bacon & Thomas, PLLC

(57) ABSTRACT

The body of a herbaceous plant, *Cistanche tubulosa* (Schenk.) Wight, is used to make a medicinal preparation containing phenylethanoid glycosides and comprising 10–70% of echinacoside by weight of the preparation and 1–40% of acteoside by weight of the preparation. The medicinal preparation is used as an active ingredient of medicinal composition for use in prevention of senile dementia, and inhibition of aggregation of blood platelets.

3 Claims, No Drawings

MEDICINAL PREPARATION CONTAINING PHENYLETHANOID GLYCOSIDES EXTRACTED FROM HERBACEOUS PLANT, *CISTANCHE TUBULOSA (SCHRENK.) WIGHT*, PROCESS OF MAKING THE SAME, AND USES OF THE SAME

FIELD OF THE INVENTION

The present invention relates generally to a medicinal preparation derived from a herbaceous plant, and more particularly to a medicinal preparation containing phenylethanoid glycosides which are extracted from a herbaceous plant belonging to the genus *Cistanche*. The preparation is used as an active ingredient of the drug capable of prevention of senile dementia and inhibition of aggregation of blood platelets. The present invention also covers a process for making the medicinal preparation as well as the uses of the medicinal preparation.

BACKGROUND OF THE INVENTION

The senior citizens are generally vulnerable to various physical and mental impairments for which there is often no panacean remedy. The senile dementia is a case in point. However, it is clinically evident that the fleshy stems of herbs belonging to the genus *Cistanche* are effective in treatment of infertility, impotency, constipation, etc. In addition, the preparation made from the fleshy stems of such perennial herbs as described above is nourishing to blood and kidney. These parasitic and perennial herbs are widely cultivated in the northwestern provinces of China and are locally known as "desert ginseng". The most abundantly cultivated species of the genus *Cistanche* is *Cistanche tubulosa* (Schenk.) Wight.

According to the systematic research done by the Japanese scientists on the chemical constituents and the pharmacological activities of the perennial herbs (genus *Cistanche*), phenylethanoid glycosides are the principal active ingredients of these perennial herbs. Such active ingredients are effective antioxidants, metabolic promoters, memory enhancers, sexuality enhancers, etc. The medicinal properties of various phenylethanoid glycoside compounds have been studied by many researchers. For such information, please refer to the following publications: Sato T., et al. Yakugaku Zasshi, 1985, 105 (12): 1131; Jimenez C., et al. Nat Prod Rep, 1994, 11 (6): 591; Cometa F., et al. Fitoterapia, 1993, 64 (3): 195.

SUMMARY OF THE INVENTION

These inventors of the present invention have had more than ten years of research experiences on the perennial herbs of the genus *Cistanche*. Among all species of the genus *Cistanche*, one species, *Cistanche tubulosa* (Schenk.) Wight, contains the greatest amount of phenylethanoid glycoside compounds. The inventors of the present invention introduce a novel process for extracting the phenylethanoid glycosides from *Cistanche tubulosa* (Schenk.) Wight, as well as a medicinal preparation containing phenylethanoid glycosides. As a result of a number of pharmacological tests conducted by these inventors of the present invention, the medicinal preparation was found to have a significant effect on memory enhancement, thrombosis prevention, inhibition of blood platelets aggregation, etc.

The primary objective of the present invention is to provide a medicinal preparation containing phenylethanoid glycosides which are extracted from a herbaceous plant, *Cistanche tubulosa* (Schenk.) Wight. It is another objective of the present invention to provide a process for making the medicinal preparation containing phenylethanoid glycosides. It is still another objective of the present invention to provide a medicinal composition for prevention of senile dementia, and a medicinal composition for prevention of aggregation of blood platelets.

The medicinal preparation of the present invention contains 10–70% of echinacoside by weight of the preparation, and 1–40% of acteoside by weight of the preparation.

Preferably, the preparation of the present invention contains 25–70% of echinacoside by weight of the preparation, and 5–40% of acteoside by weight of the preparation.

Preferably, the medicinal preparation of the present invention is made from the fleshy stems of *Cistanche tubulosa* (Schenk.) Wight.

Preferably, the medicinal preparation of the present invention further contains 2'-acetylacteoside; campneoside I; campneoside II; cistantubuloside A, $B_1$, $B_2$, $C_1$, $C_2$; crenatoside; decaffeoylacteoside; isoacteoside; rhodioloside; syringalide A; 3'-α-L-rhamnopyranoside, and tubuloside A, with each in an amount less than 5% by weight of the medicinal preparation.

The process of the present invention for making the medicinal preparation involves a first step in which the subterranean portions of *Cistanche tubulosa* (Schenk.) Wight are extracted by a first polar solvent. The extract so obtained is then introduced into a column which is packed with hydrophobic macro-porous polymeric beads, thereby enabling phenylethanoid glycosides to be adsorbed on the polymeric beads. The relatively less strongly adsorbed compounds are then eluted from the column by use of a second polar solvent serving as a mobile phase, with most of phenylethanoid glycosides still being adsorbed on the polymeric beads. Finally, phenylethanoid glycosides are eluted from the column by use of a third polar solvent so as to obtain an eluate which contains phenylethanoid glycosides. The third polar solvent is lower in polarity than the second polar solvent.

Preferably, the subterranean portions of *Cistanche tubulosa* (Schenk.) Wight are fleshy stems. The subterranean portions which are mixed with the first polar solvent, and the resulting mixture is then cooked to boil for a period lasting 0.5–10 hours. The mixture is subsequently filtered so as to obtain a solution. The solution is an extract, which may be in a concentrated form by decompression. Preferably, the mixture contains the subterranean portions of *Cistanche tubulosa* (Schenk.) Wight and the first polar solvent in a weight ratio ranging from 1:4 to 1:20. Preferably, the first polar solvent is either water, or a mixed solvent containing water and ethyl alcohol. Preferably, the polymeric bead of the column used in the process of the present invention is a cross-linked polyaromatics. More preferably, the polymeric bead is formed of cross-linked polystyrene, or a cross-linked copolymer of styrene and divinyl benzene. Preferably, the second polar solvent is water. Preferably, the third polar solvent is methanol, ethanol, a water-methanol mixture, or a water-ethanol mixture. More preferably, the third polar solvent is a mixture of water and ethanol.

The process of the present invention further comprises removing the solvent that is contained in the eluate so produced, thereby resulting in production of a dry preparation.

The preparation of the present invention can be used to make a medicinal composition for prevention of senile dementia. The medicinal composition contains a therapeutically effective amount of the preparation as an active ingredient and a pharmaceutically acceptable carrier or diluent for the active ingredient.

The preparation of the present invention can also be used to make a medicinal composition for inhibition of blood platelets aggregation. The medicinal composition contains a therapeutically effective amount of the preparation and a medicinally-allowable carrier or diluent. The preparation is used as an active ingredient of the compound.

side by weight of the preparation, and 1–40% of acteoside by weight of the preparation. The phenylethanoid glycoside compounds derived from *Cistanche tubulosa* (Schenk.) Wight have the following chemical structure:

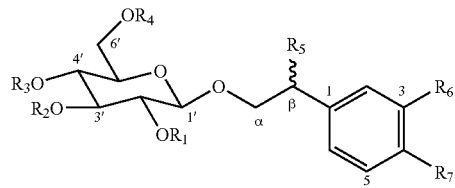

and include 2'-acetylacteoside; campneoside I; campneoside II; cistantubuloside A, $B_1$, $B_2$, $C_1$, $C_2$; crenatoside; decaffeoylacteoside; isoacteoside; rhodioloside; syringalide A; 3'-α-L-rhamnopyranoside, and tubuloside A shown in Table 1, in which most of the compounds are in a minute or trace amount in the preparation except echinacoside and acteoside.

TABLE 1 principal ingredients of the preparation

| Ingredient | $R_1$ | $R_2$ | $R_3$ | $R_4$ | $R_5$ | $R_6$ | $R_7$ |
|---|---|---|---|---|---|---|---|
| 2'-Acetylacteoside | Ac | Rha | Cf | H | H | OH | OH |
| Acteoside | H | Rha | Cf | H | H | OH | OH |
| Campneoside I | H | Rha | Cf | H | OMe(S/R) | OH | OH |
| Campneoside II | H | Rha | Cf | H | OH(S/R) | OH | OH |
| *Cistantubuloside A | H | Rha | Cf | Glc | H | H | OH |
| *Cistantubulosides $B_1/B_2$ | H | Rha | Cm/c-Cm | Glc | H | OH | OH |
| *Cistantubulosides $C_1/C_2$ | H | Rha | Cf | Glc | OH(S/R) | OH | OH |
| Decaffeoylacteoside | H | Rha | H | H | H | OH | OH |
| Echinacoside | H | Rha | Cf | Glc | H | OH | OH |
| Isoacteoside | H | Rha | H | Cf | H | OH | OH |
| Rhodioloside (Salidroside) | H | H | H | H | H | H | OH |
| Syringalide A 3'-α-L-rhamnopyrano side | H | Rha | Cf | H | H | H | OH |
| Tubuloside A | Ac | Rha | Cf | Glc | H | OH | OH |
| Crenatoside | | | | See following structure | | | |

*new compound
Ac: Acetyl
Cf: trans-Caffeoyl
Cm: trans-Coumaroyl
c-Cm: cis-Coumaroyl
Glc: β-D-Glucopyranose
Rha: α-L-Rhamnopyranose The present invention also discloses a method of treating and preventing an individual suffering senile dementia comprising administering to the individual a therapeutically effective amount of the preparation of the present invention.

The present invention further discloses a method of inhibiting blood platelets aggregation in an individual comprising administering to the individual a therapeutically effective amount of the preparation of the present invention.

DETAILED DESCRIPTION OF THE INVENTION

The present invention provides a preparation containing phenylethanoid glycoside compounds from *Cistanche tubulosa* (Schenk.) Wight, which contains 10–70% of echinaco-

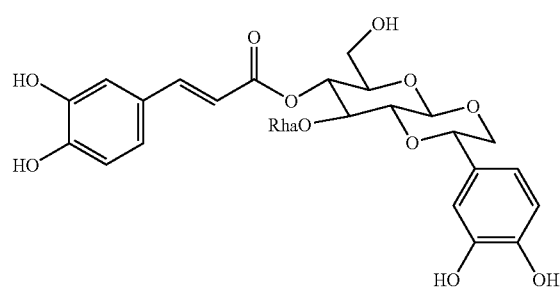

crenatoside

All the compounds listed in Table 1 were verified by means of a high performance liquid chromatography, which was obtained under the following conditions: stationary phase being silicone of C18 alkyl silane; mobile phase being acetonitrile-0.05M phosphoric acid aqueous solution (gradient eluting (4:96→15:85)), flow rate of 1 ml/min, and detecting wavelength of 330 nm.

The process of making the medicinal preparation of the present invention is explicitly described hereinafter. The process of the present invention involves two steps, which are extraction and purification. In the first step, the fleshy stems of *Cistanche tubulosa* (Schenk.) Wight are cut into flakes or are comminuted into fine particles or powder. The flakes or fine particles are then soaked in a medium which is water, ethanol, methanol, or low fatty alcohol. The extraction is carried out at room temperature. The filtrate is concentrated in vacuo, thereby resulting in formation of an extract. The purification of the extract is done by heating the extract in water before the extract is transferred to an adsorption column packed with macro-porous adsorption resin of D-101 type or AB-8 type. The column is eluted with water, methanol, ethanol, a water-containing methanol, or a water-containing ethanol, etc. The eluting may be carried out with a solution of a constant concentration or solutions of gradient concentrations. The eluate is collected, concentrated and then dried by a conventional drying method. Upon completion of the drying of the eluate, the medicinal preparation of the present invention is obtained. The medicinal preparation so produced contains phenylethanoid glycosides and is used for making medicinal compositions for use in prevention of senile dementia, or in inhibition of aggregation of blood platelets.

The pharmacological test of the medicinal preparation of the present invention was carried out by a so-called "water maze experiment", in which a test group of small mice was provided with a diet containing the medicinal preparation of the present invention. In comparison with the control group, the learning memory of the small mice of the test group were enhance, the memory loss of the test group due to ethanol or drugs was apparently reduced. Similarly, a group of rats was provided with a diet containing the medicinal preparation of the present invention. By comparison, these rats were found to be less vulnerable to thrombosis, or aggregation of blood platelets. On the basis of the results of the pharmacological test described above, a clinical test may be carried out to study the effect of the medicinal preparation of the present invention on prevention and treatment of senile dementia, including VD and AD.

The extraction, purification, and pharmacological effect of the medicinal preparation of the present invention will be further explained by referring to the following nonrestrictive embodiments and comparative experiments.

EXTRACTION

EMBODIMENT 1

10 kg of the flakes of fleshy stems of *Cistanche tubulosa* (Schenk.) Wight was soaked in water in an amount which was 8 times of the flakes. The flakes was soaked in the water for one hour before being decocted with the water for two hours. The decocted mixture was filtered to obtain a first filtrate. The residue was then decocted with the water in an amount which was 6 times of the residue and the decocted mixture was filtered to obtain a second filtrate. A third filtrate was also obtained by the same procedures as the second filtrate. The three filtrates were combined and concentrated in vacuo to have a specific gravity of 1.10 (50° C.). The filtrate in the concentrated form was mixed with ethanol to form a mixture containing 60% of the ethanol, which was then refrigerated for 12 hours. Thereafter, a supernatant was harvested from the cooled mixture while the residue was filtered to obtain a filtrate, which was combined with the supernatant to form an end extract. The end extract was concentrated in vacuo to have a specific gravity of 1.10 (50° C.), in which the ethanol was recycled. The end extract so produced has a weight of 5.6 kg.

EMBODIMENT 2

10 kg of the fleshy stems of *Cistanche tubulosa* (Schenk.) Wight in the powder form was soaked in water in an amount which was 15 times of the powder for 2 hours, and was then decocted for 3 hours. Thereafter, the decocted mixture was filtered to obtain a first filtrate, while the residue of the decocted mixture was mixed with water in an amount which was 12 times of the residue, decocted for 2 hours and filtered to obtain a second filtrate. The procedures were repeated two additional times to obtain a third filtrate and a fourth filtrate. The four filtrates were combined and concentrated in vacuo to have a specific gravity of 1.25 (50° C.). The filtrate in the concentrated form was mixed with ethanol to form a mixture containing 80% of the ethanol, which was then refrigerated for 24 hours. Thereafter, a supernatant was harvested from the cooled mixture while the residue was filtered to obtain a filtrate, which was combined with the supernatant to form an end extract. The end extract was concentrated in vacuo to have a specific gravity of 1.25 (50° C.), in which the ethanol was recycled. The end extract so produced has a weight of 7.2 kg.

EMBODIMENT 3

10 kg of the flakes of fleshy stems of *Cistanche tubulosa* (Schenk.) Wight was soaked in water in an amount which was 7 times of the flakes. The flakes was soaked in the water for three hours before being decocted with the water for four hours. The decocted mixture was filtered to obtain a first filtrate. The residue was then decocted with the water in an amount which was 5 times of the residue and the decocted mixture was filtered to obtain a second filtrate. A third filtrate and a fourth filtrate were also obtained by the same procedures as the second filtrate. The four filtrates were combined and concentrated in vacuo to have a specific gravity of 1.05 (50° C.). The filtrate in the concentrated form was mixed with ethanol to form a mixture containing 50% of the ethanol, which was then refrigerated for 10 hours. Thereafter, a supernatant was harvested from the cooled mixture while the residue was filtered to obtain a filtrate, which was combined with the supernatant to form an end extract. The end extract was concentrated in vacuo to have a specific gravity of 1.10 (50° C.), in which the ethanol was recycled. The end extract so produced has a weight of 6.5 kg.

EMBODIMENT 4

10 kg of the fleshy stems of *Cistanche tubulosa* (Schenk.) Wight in the powder form was soaked in 40% ethanol in an amount which was four times of the powder for 3 hours, and was then decocted under refluxing for 3 hours. Thereafter, the decocted mixture was filtered to obtain a first filtrate, while the residue of the decocted mixture was mixed with 40% ethanol in an amount which was four times of the residue, decocted for four hours and filtered to obtain a second filtrate. The procedures were repeated two additional times to obtain a third filtrate and a fourth filtrate. The four filtrates were combined and concentrated in vacuo to have a specific gravity of 1.05 (50° C.), thereby resulting in production of an end extract having a weight of 6.2 kg.

PURIFICATION

EMBODIMENT 5

6 kg of the end extract was dissolved in water with heating, which was in an amount of one half of the end extract. The extract solution was then applied into an adsorption column packed with pretreated macro-porous adsorption resin of the D-101 type. The column was first eluted with water to yield a water eluate in the amount of two times of the fleshy stems, and was than eluted with 20% ethanol to yield a first 20% ethanol eluate in the amount of two times of the fleshy stems. The water eluate was subjected to another round of the adsorption-desorption operations to obtain a second ethanol eluate. The two 20% ethanol eluates were combined, concentrated, and dried to yield a preparation containing phenylethanoid glycosides and having a weight of 865 g.

The contents of echinacoside and acteoside were measured by a high performance liquid chromatography (HPLC), with the stationary phase being silicone of C18 alkyl silane, with the mobile phase being methanol-0.15% acetic acid (30:70), with the flow rate of 1 ml/min, and with the detecting wavelength of 333 nm.

The echinacoside and the acteoside dried at 60° C. in vacuo for 24 hours were measured and dissolved in 50% methanol to prepare reference solutions, with each 1 ml solution containing 0.1 mg of the solute.

The test solution was prepared by dissolving 50 mg of the preparation containing phenylethanoid glycosides in an appropriate amount of 50% methanol in a 25 ml-graduated container while sonicating. More 50% methanol was added to the resulting solution until the 25 ml mark of the contained was reached. The solution in amount of 1 ml was taken accurately and was transferred to a 10 ml-graduated container into which 50% methanol was added to the mark. The test solution was obtained after the solution was filtered by a 0.45 μm membrane.

The reference solution and the test solution were each taken out in an amount of 5 μL and were injected into the liquid chromatography column, and the peak areas of the echinacoside and the acteoside were measured. The contents were calculated by using the peak areas. The content of the echinacoside is 37.5% while the content of the acteoside is 6.7% by weight of the preparation.

EMBODIMENT 6

6 kg of the end extract was dissolved in water with heating, which was in an amount of five times of the end extract. The extract solution was then applied into an adsorption column packed with pretreated macro-porous adsorption resin of the AB-8 type. The column was first eluted with water to yield a water eluate in the amount of eight times of the fleshy stems, and was than eluted with 60% ethanol to yield a first 60% ethanol eluate in the amount of eight times of the fleshy stems. The water eluate was subjected to another round of the adsorption-desorption operations by eluting the column with water in the amount of six times of the fleshy stems and with 60% ethanol in sequence to obtain a second ethanol eluate in the amount of seven times of the fleshy stems. The two 60% ethanol eluates were combined, concentrated, and dried to yield a preparation containing phenylethanoid glycosides and having a weight of 1203 g.

By using the HPLC method described in the Embodiment 5, the contents of echinacoside and acteoside are found to be respectively 48.6% by weight, and 11.8% by weight of the preparation.

EMBODIMENT 7

6 kg of the end extract was dissolved in water with heating, which was in an amount of three times of the end extract. The extract solution was then applied into an adsorption column packed with macro-porous adsorption resin of the AB-8 type. The column was first eluted with water to yield a water eluate in the amount of eight times of the fleshy stems, and was than eluted with 95% ethanol to yield a first 95% ethanol eluate in the amount of eight times of the fleshy stems. The water eluate was subjected to another round of the adsorption-desorption operations by eluting the column with water in the amount of six times of the fleshy stems and with 95% ethanol in sequence to obtain a second ethanol eluate in the amount of eight times of the fleshy stems. The two 60% ethanol eluates were combined, concentrated, and dried to yield a preparation containing phenylethanoid glycosides and having a weight of 1260 g.

By using the HPLC method described in the Embodiment 5, the contents of echinacoside and acteoside are found to be respectively 41.3% by weight, and 7.4% by weight of the preparation.

EMBODIMENT 8

6 kg of the end extract was dissolved in water with heating, which was in the same amount of the end extract. The extract solution was then applied into an adsorption column packed with macro-porous adsorption resin. The column was first eluted with water to yield a water eluate in the amount of four times of the fleshy stems, and was than eluted with 40% ethanol to yield a first 40% ethanol eluate in the amount of five times of the fleshy stems. The water eluate was subjected to another round of the adsorption-desorption operations by eluting the column with water in the amount of three times of the fleshy stems and with 40% ethanol in sequence to obtain a second ethanol eluate in the amount of four times of the fleshy stems. The two 40% ethanol eluates were combined, concentrated, and dried to yield a preparation containing phenylethanoid glycosides and having a weight of 1107 g.

By using the HPLC method described in the Embodiment 5, the contents of echinacoside and acteoside are found to be respectively 31.7% by weight, and 6.1% by weight of the preparation.

PHARMACOLOGICAL EFFECTS

EMBODIMENT 9

The medicinal preparation of the present invention was used in a water maze experiment to study its effect on the learning memory of LACA mice. The Piracetam Tablets was used as a positive comparative drug for testing 6 days per week. The test lasted for 27 days. The test results are listed in Table 2.

the control group and the doped groups, which were respectively doped with 50 mg/kg of the preparation containing phenylethanoid glycosides, 200 mg/kg of the preparation containing phenylethanoid glycosides, and 400 mg/kg of the preparation containing phenylethanoid glycosides. The period when the response time shows meaningful difference by d value analysis for the 50 mg/kg group is 9 days; for the 200 mg/kg group is 13 days; and for the 400 mg/kg group is 27 days. The period when the response time shows meaningful difference increases as the dosage increases. In addition, the period when the response time shows meaningful difference for the positive control group (Piracetam group) is 7 days, which is shorter than that of the doped group of 400 mg/kg, and thus Piracetam Tablets are less effective on the learning memory of mice compared to the preparation of the present invention.

EMBODIMENT 10

The effect of the preparation of the present invention on the prevention of memory loss by the LACA mice was studied by the water maze experiment. The mice were orally

TABLE 2

Effect on the leaning memory of mice by administering the preparation of the present invention orally

| Test | Comparison groups | d value (n = 27) | | | | | |
|---|---|---|---|---|---|---|---|
| | | ≧0.5 | | ≧0.8 | | ≧0.5 sum | |
| | | day | % | day | % | day | % |
| First time | Control group - Group provided with 50 mg/kg of preparation containing phenylethanoid glycosides | 4 | 14.8 | 5 | 18.5 | 9 | 33.3 |
| | Control group - Group provided with 200 mg/kg of preparation containing phenylethanoid glycosides | 10 | 37.0 | 3 | 11.1 | 13 | 48.2 |
| Second time | Control group - Group provided with 400 mg/kg of reparation containing phenylethanoid glycosides | 0 | 0 | 27 | 100.0 | 27 | 100.0 |
| | Control group - Positive comparative group provided with 400 mg/kg of Piracetam | 5 | 18.5 | 2 | 7.4 | 7 | 25.5 |
| | Piracetam group - Group provided with 400 mg/kg of reparation containing phenylethanoid glycosides | 7 | 25.9 | 16 | 59.3 | 23 | 85.2 |

According to the data listed in the Table 2, it is readily apparent that the preparation of the present invention has a meaningful effect on the learning memory of the mice, as exemplified by the difference in the response time between administered with the drugs. One hour after such an oral administration, they were provided with 30% ethanol 0.1 ml/10 g BW. In 30 minutes, the water maze experiment was started. The results of the swimming performance of the mice were listed in Table 3.

TABLE 3

The effect of the preparation containing phenylethanoid
glycoside one-week orally administered on the prevention
of memory loss of LACA mail mice induced by ethanol

| Group | Dose (mg/kg) | Number of animal | Arrival at destination after being trained | | Arrival at destination after being given alcohol | | | |
|---|---|---|---|---|---|---|---|---|
| | | | Time (second) | Error number/ error number of animal | Time (second) | Error number/ error number of animal | Error rate, times/ number of animal | Group error rate, times/number of animal |
| Preparation of the present invention | 50 | 12 | 7.46 ± 0.13 | 0/0 | 34.40 ± 21.71* | 47/8 | 5.88 | 3.92 |
| | 200 | 11 | 7.14 ± 0.18 | 0/0 | 16.99 ± 9.06## | 8/3ΔΔ | 2.67 | 0.73 |
| | 400 | 10 | 7.91 ± 0.19 | 0/0 | 24.38 ± 27.84 | 46/7 | 6.57 | 4.60 |
| Piracetam | 400 | 10 | 8.00 ± 0.46 | 0/0 | 24.08 ± 32.52 | 54/6 | 9.00 | 5.40 |
| control | | 12 | 7.73 ± 0.75 | 0/0 | 37.78 ± 15.90 | 62/10 | 6.20 | 5.17 | t study: comparison with the comparative group ## $P < 0.01$,
comparison with the 200 mg/kg group * $p < 0.05$
$X^2$ study: comparison with the comparative group ΔΔ $P < 0.01$ According to the data listed in Table 3, the medicinal preparation of the present invention is more effective in prevention of memory loss of the mice as compared with Piracetam. The arrival time of the group provided with the preparation of the present invention is shorter than that of the Piracetam group, after the mice were provided with ethanol. The difference between the preparation 200 mg/kg group and the control group is P<0.01. The difference between the preparation 50 mg/kg group and the preparation 200 mg/kg group is P<0.05. As a result, the does of the preparation is a factor. There is no significant difference among the preparation 400 mg/kg group, the Piracetam group, and the control group, thereby indicating that the dose of 200 mg/kg is most effective in prevention of memory loss. On the basis of the "error" data listed in Table 3, the does of 200 mg/kg is most effective in prevention of memory loss.

EMBODIMENT 11

A study was done on the effect of the preparation of the present invention on the memory gaining difficulty of the mice caused by Hyosine.

(1) Drug and Animal

The test drug and the comparative drug were identical with those of the Embodiment 9. The mice were grouped randomly into the normal comparative group, the model group, the Piracetam 600 mg/kg group, and the preparation groups 400 mg/kg, 200 mg/kg, 100 mg/kg. Each group contains 15 mice. The drugs were administered on the basis of 0.2 ml/10 g body weight. The jumping training was started on the completion of the $29^{th}$ day administration. The drug was given one hour before training. With the exception of the normal comparative group, each group was provided with a belly cavity injection of Hyosine in amount of 1 mg/kg. The test was done on the $30^{th}$ day, and the drug was given one hour before training. The results are listed on Table 4.

TABLE 4

The effect of phenylethanoid glycoside
containing preparations on the mice memory
gaining difficulty caused by hyosine (X ± SD)

| group | dose (mg/kg) | animal number | test latent (S) | frequency of test error (times/5 min) |
|---|---|---|---|---|
| control group | | 14(1) | 194.1 ± 101.5* | 1.36 ± 1.45* |
| model group | | 15 | 67.1 ± 78.4 | 3.13 ± 2.47 |
| Piracetam group | 600 | 15 | 144.5 ± 117.4* | 1.60 ± 1.40* |
| preparations of the present invention | 400 | 12(3) | 206.1 ± 98.8** | 1.08 ± 1.16** |
| | 200 | 12(3) | 183.2 ± 115.2** | 1.42 ± 1.38* |
| | 100 | 14(1) | 191.8 ± 117.5** | 1.50 ± 2.07 | comparison with the model group,
*$p < 0.05$,
**$p < 0.01$;
the parenthesized numeral indicates the number of death caused by electric shock.

According to the data listed in Table 4, the test latent periods of the groups are shortened as compared with the normal comparative group. However, the frequency of the test error increases. As compared with the model group, the Piracetam 600 mg/kg group and the preparation groups 400 mg/kg, 200 mg/kg have a protracted latent period and a reduction in frequency of test error, thereby indicating a memory improvement. The preparation 100 mg/kg group has a protracted latent period, and an error frequency which is not different from that of the model group.

EMBODIMENT 12

A study was done on the effect of the preparation of the present invention on thrombosis of the vein bypass of the rats.

The male SD rats were studied as compared with the aspirin.

The results are listed in Table 5.

Thrombosis inhibition rate (%)=(distilled water comparative group thrombosis weight–drug group thrombosis weight)/distilled water comparative group thrombosis weight×100%.

TABLE 5

The effect of the preparation containing
phenylethanoid glycoside administered
orally on thrombosis of the vein bypass of rats

| Group | dose (mg/kg) | number of animal | thrombosis weight (mg, x ± SD) | thrombosis inhibition rate (%) |
|---|---|---|---|---|
| distilled water | | 10 | 44.9 ± 3.83 | |
| aspirin | 100 | 10 | 29.2 ± 4.00** | 34.97 |
| preparation | 200 | 10 | 37.7 ± 7.42* | 16.04 |
| | 100 | 10 | 36.1 ± 5.16* | 19.60 |
| | 50 | 10 | 42.6 ± 7.12 | 5.12 | comparison with the distilled water comparative group
*p < 0.05,
**p < 0.01.

On the basis of the data listed in Table 5, the preparations 200 mg/kg and 100 mg/kg are capable of inhibiting the thrombosis of the vein bypass of the rats, as compared with the distilled water comparative group, with the inhibition rates being respectively 16.04%, 19.60%. However, the effects of the preparations are weaker than that of the aspirin 100 mg/kg which has an inhibition rate of 34.97%. The preparation 50 mg/kg has no effect on the thrombosis formation.

EMBODIMENT 13

A study was done on the effect of the preparation of the present invention on aggregation of blood platelets of the rats.

The aggregation of blood platelets was caused by using adenosine disodium diphosphate (ADP). 1 mg/ml ADP solution was kept refrigerated before use. When the ADP solution was about to be used, it was diluted three times with the phosphoric acid buffer solution.

The male SD rats were randomly divided into five groups in accordance with the body weight. These five groups were the distilled water comparative group, the aspirin group, the 200 mg/kg preparation group, the 100 mg/kg preparation group, and the 50 mg/kg preparation group. The drugs were orally administered, with the administration volume being 0.5 mg/100 g. The rats of the distilled water comparative group were given distilled water in same quantity. The administration continued for 7 days. The rats were not fed for 12 hours prior to the final administration. One hour after the final administration the blood was drawn out from the main artery. The blood so draw out was prevented from aggregation by 3.8% sodium citrate (1:9). The blood sample was centrifuged at 1000 rpm for three minutes to facilitate the removing of the plasma rich in blood platelets (PRP). The remainder of the blood sample was further centrifuged at 300 rpm for 10 minutes to facilitate the separating of the plasma poor in blood platelets (PPP). 200 µL PRP was introduced into an opacity-comparison tube and the opacity thereof was adjusted to zero point with the PPP. The mixture was incubated for 5 minutes before adding thereinto 50 µL of the ADP solution for causing the aggregation of blood platelets. The aggregation degree was determined by using a SPA-4 multifunctional blood platelet aggregation meter. The inhibition rate of the blood platelet aggregation is calculated by the following formula.

Inhibition rate (%)=(control group maximum aggregation degree−experimental group maximum aggregation degree)/(control group maximum aggregation degree)×100%

The results of the test are listed in Table 6. It is readily apparent that the preparations (200 mg/kg, 100 mg/kg, 50 mg/kg) are capable of inhibiting the aggregation of blood platelets, and that the preparation (200 mg/kg) has the highest inhibition rate of 59.48%.

TABLE 6

The effect of preparation containing
phenylethanoid glycosides orally administered
on blood platelets aggregation of rats

| group | dose (mg/kg) | number of rats | maximum aggregation(%) (*±SD) | aggregation inhibition (%) |
|---|---|---|---|---|
| Distilled water group | | 10 | 54.82 ± 7.88 | |
| Aspirin group | 100 | 11 | 32.73 ± 11.14** | 40.30 |
| preparation | 200 | 10 | 22.21 ± 6.23** | 59.48 |
| | 100 | 11 | 34.54 ± 15.69* | 36.99 |
| | 50 | 10 | 31.65 ± 12.81** | 42.26 |

Comparison with the distilled water group
*P < 0.01,
**P < 0.001

What is claimed is:

1. A method of treating an individual suffering from senile dementia comprising administering to the individual suffering from senile dementia a therapeutically effective amount of a medicinal preparation containing phenylethanoid glycosides extracted from *Cistanche tubulosa* (Schenk.) Wight, said preparation comprising 10–70% of echinacoside by weight of said preparation, and 1–40% of acteoside by weight of said preparation.

2. The method as defined in claim 1, wherein the preparation comprises 25–70% of echinacoside by weight of said preparation, and 5–40% of acteoside by weight of said preparation.

3. The method as defined in claim 1, wherein the preparation is extracted from fleshy stems of *Cistanche tubulosa* (Schenk.) Wight.

* * * * *